United States Patent [19]
Parker, III

[11] Patent Number: 5,846,250
[45] Date of Patent: Dec. 8, 1998

[54] SURGICAL TOOL

[76] Inventor: Augustus G. Parker, III, 6233 Windbrook Dr., Blacklick, Ohio 43004

[21] Appl. No.: 855,340

[22] Filed: May 13, 1997

[51] Int. Cl.⁶ .............................. A61B 17/42; A61B 17/34
[52] U.S. Cl. ............................................. 606/125; 606/185
[58] Field of Search .................. 606/1, 125, 167, 606/171, 184, 185; 132/321, 329; 433/141, 143

[56] References Cited

U.S. PATENT DOCUMENTS

| | | | |
|---|---|---|---|
| 1,451,380 | 4/1923 | Thum | 132/329 |
| 2,521,161 | 9/1950 | Grover | 606/167 |
| 3,749,099 | 7/1973 | Cotey | 606/125 |
| 4,357,945 | 11/1982 | Janko | 606/125 |
| 4,805,646 | 2/1989 | Shimenkov | 132/329 |

*Primary Examiner*—Glenn K. Dawson
*Attorney, Agent, or Firm*—Kremblas, Foster, Millard & Pollick

[57] ABSTRACT

An amniotic membrane perforator tool having a tip portion, a shaft portion, a flexing portion, and a handle portion. The shaft portion is adjacent the tip portion and is preferably of a generally T-shaped cross-section having a vertical component and a horizontal component. The shaft portion is intermediate the tip portion and the flexing portion. The flexing portion is intermediate the shaft portion and the handle portion, and includes at least one crest and at least one valley. The shaft portion is pivotable at the flexing portion relative to the handle portion. The handle portion is dimensioned such that the handle portion is wider than high. Furthermore, the handle portion preferably includes a plurality of ribs.

15 Claims, 2 Drawing Sheets

SURGICAL TOOL

CLAIM TO PRIORITY

This application claims the benefit of provisional application 60/017,280, which application was filed on May 13, 1996.

FIELD OF THE INVENTION

This invention relates to a surgical tool, and more particularly to an amniotic membrane perforator.

BACKGROUND OF THE INVENTION

In the practice of obstetrics, it is frequently necessary, in order to facilitate the delivery process, to rupture the amniotic membrane so that fluids trapped therein can be expelled. This happens quite often without requiring the help of the attending doctor, and is only in those cases where the membrane fails to rupture naturally that the doctor is called to artificially rupture or perforate the chorioamniotic membrane. When the chorioamniotic membrane is perforated, the release of water increases the level of prostaglandins, which in turn assists in the progress of labor.

Various devices have been used in the past for rupturing amniotic membranes, many of which have been fashioned and constructed by the doctor from his supply of surgical instruments and from other devices. For the most part, however, the devices that have been used for this purpose have been relatively cumbersome and difficult to operate and use, are not designed for this specific operation, or are relatively expensive and must be resterilized after each use. Such known devices are also usually relatively large and often difficult to insert into the vagina, they are difficult to properly locate, and frequently are difficult to manipulate into the best possible position to perform the desired operation.

Many of the known devices are so constructed that they have pointed or sharp end portions extending in the direction of the unborn child, therefore creating the considerable possibility of danger or injury to the child. Furthermore, if some of the known devices become accidentally lodged in the fetal or maternal tissue and the doctor pulls outwardly believing he has hooked the amniotic membrane, the tear created and the resulting damage caused could be severe. This could, for example, result in hemorrhaging, infection, scarring, as well as other forms of injury to the child and/or to the mother. One such prior art device featured a glove with a small hook at the end of one of the glove's fingers. One obvious drawback in addition to those discussed above was that the effectiveness of the device was dependent on the operator's fingers being long enough to reach the membrane.

Concerns relating to the accidental puncturing or tearing of tissue are addressed in U.S. Pat. Nos. 3,410,269; 4,462,376; and 4,807,625. One of the most popular amniotic membrane perforators is sold by Hollister Incorporated under the trademark Amnihook®. This device is shown in U.S. Pat. No, 3,624,747. The inventors of that particular surgical instrument also were awarded U.S. Pat. No. 3,533,411. Although the Amnihook® amniotic membrane perforator enjoys a sizeable market share, current competitors still exist, such as the Amni-Perf™ amniotic membrane perforator manufactured by Centurion Hospital Products, and Amniotome™ manufactured by Galenica, Inc. There is also the amniotic membrane perforator disclosed in U.S. Pat. No. 5,087,262.

In many of the amniotic membrane perforators discussed above, the plastic shaft associated with the surgical tools is relatively inflexible. Thus, as the medical professional attempts to guide the membrane perforator into position such that it can rupture the chorioamniotic membrane, it is not uncommon for significant pain and/or bruising to occur. Even in existing perforators where the shaft is bent at a predetermined fixed angle, in an attempt to lessen the pain and/or bruising, the predetermined fixed angle may not correspond to the orientation of the patient's anatomy.

Furthermore, in diabetic patients the use of a relatively inflexible straight tool which can cause bleeding of any sort, such as hematomas, is not advisable. Still further, in patient's whose amniotic membrane is positioned above and behind the pubic bone the use of a relatively inflexible straight tool is precluded.

From the foregoing discussion it can be appreciated that many women who have required an amniotic membrane perforator be used in connection with their giving birth would not characterize the procedure in favorable terms, due to the pain and/or bruising which typically accompanies the use of current amniotic membrane perforators. It is thus apparent that the need exists for an improved amniotic membrane perforator or the like for use in childbirth.

SUMMARY OF THE INVENTION

In accordance with this invention a surgical tool is provided, and more specifically, an amniotic membrane perforator. This invention is formed of plastic, and includes a tip portion, a shaft portion, flex means, and a handle portion. The tip portion has a hook. The shaft portion is adjacent to the tip portion, and intermediate the tip portion and the flex means. Preferably the shaft portion is of a generally T-shaped cross-section, with the shaft portion having a vertical component and a horizontal component. The flex means is intermediate the shaft portion and the handle portion, with the shaft portion being pivotable at the flex means relative to the handle portion.

The amniotic membrane perforator tool of this invention has a flex means including at least one crest and at least one valley. More preferably the flex means comprises a plurality of crests and valleys. Additionally, the handle portion is wider than said handle portion is high, and preferably includes a plurality of ribs. More preferably the handle portion has a top surface having a plurality of ribs. Still more preferably the handle portion has a bottom surface having a plurality of ribs. Most preferably the handle portion has a top surface and a bottom surface with the top surface and the bottom surface each having a plurality of ribs.

There is also disclosed an amniotic membrane perforator tool having a tip portion having a hook, a shaft portion adjacent the tip portion, flex means comprising at least one crest and at least one valley with the shaft portion being intermediate the tip portion and the flex means, and a handle portion wider than the handle portion is high, with the flex means being intermediate the shaft portion and the handle portion. The shaft portion is of a generally T-shaped cross-section, with the shaft portion having a vertical component and a horizontal component. The shaft portion is pivotable at the flex means relative to the handle portion. More preferably the flex means comprises a plurality of crests and valleys.

The handle portion includes a plurality of ribs. Preferably O the top surface of the handle portion has ribs. The bottom surface of the handle portion may also have ribs. Most preferably the top surface and the bottom surface each have a plurality of ribs.

There is also disclosed an amniotic membrane perforator tool having a tip portion having a hook, a shaft portion adjacent the tip portion with the shaft portion being of a generally T-shaped cross-section, such that the shaft portion has a vertical component and a horizontal component, flex means comprising at least one crest and at least one valley with the shaft portion being intermediate the tip portion and the flex means, and a handle portion.

The handle portion is dimensioned such that it is wider than high, and such that it includes a plurality of ribs. The flex means are intermediate the shaft portion and the handle portion, and the shaft portion is pivotable at the flex means relative to the handle portion.

The primary objective of this invention is to provide an improved amniotic membrane perforator that does not cause the pain or bruising associated with most amniotic membrane perforators.

Another object of the invention is to provide a tool which is relatively inexpensive and simple to fabricate.

Still another object of the invention is to provide a tool which is easy to use.

Yet still another object of the invention is to provide a tool which may allow an amniotomy to be performed earlier in labor.

These and other objects and advantages of this invention will be readily apparent from the following detailed description of an illustrative embodiment thereof, the accompanying drawings, and the appended claims.

DETAILED DESCRIPTION OF THE INVENTION

Figure 1:
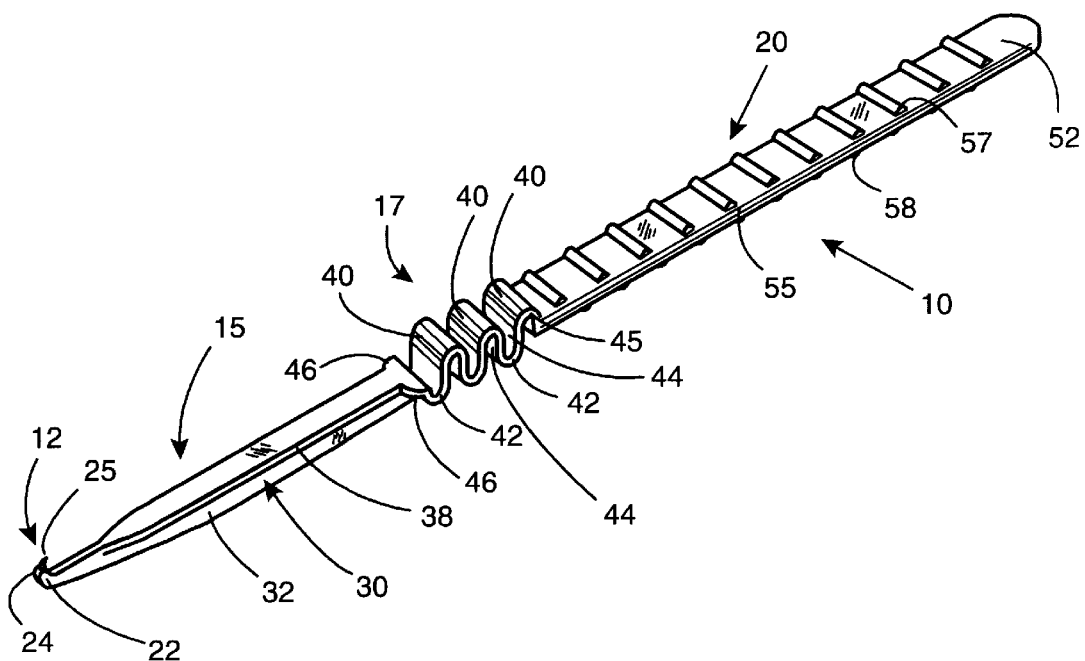
FIG. 1. discloses a perspective view of an amniotic membrane perforator made in accordance with the present invention.
Figure 2:
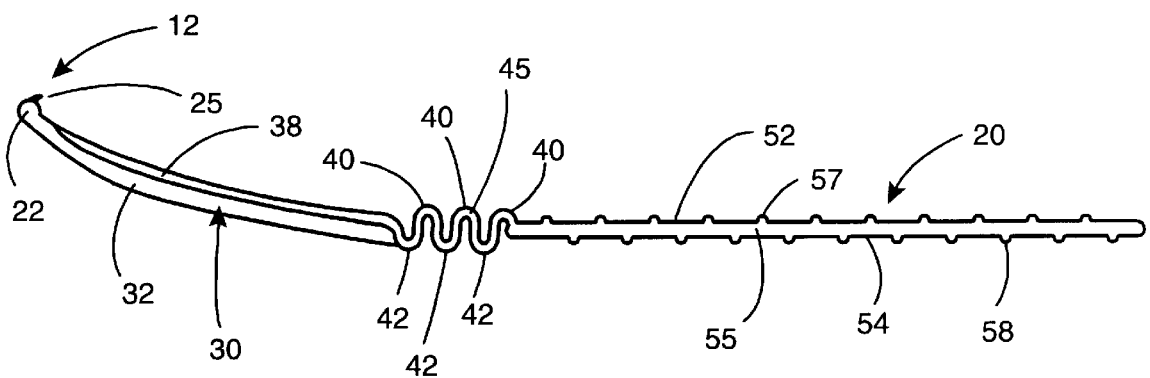
FIG. 2 discloses a side elevational view of the invention.
Figure 3:
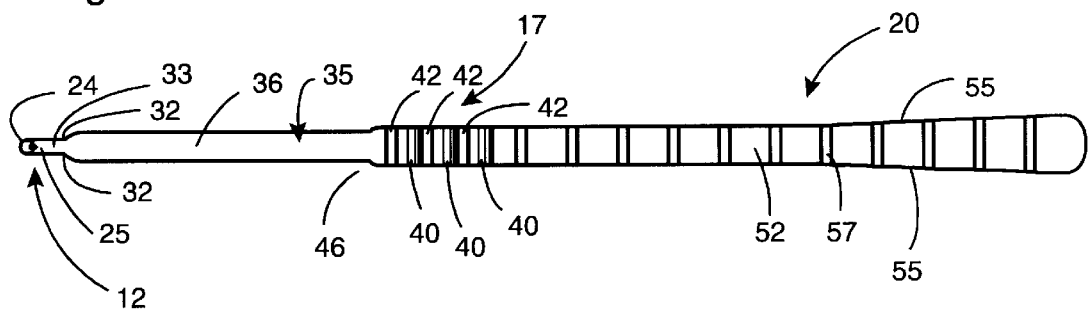
FIG. 3 discloses a top plan view of the invention.
Figure 4:
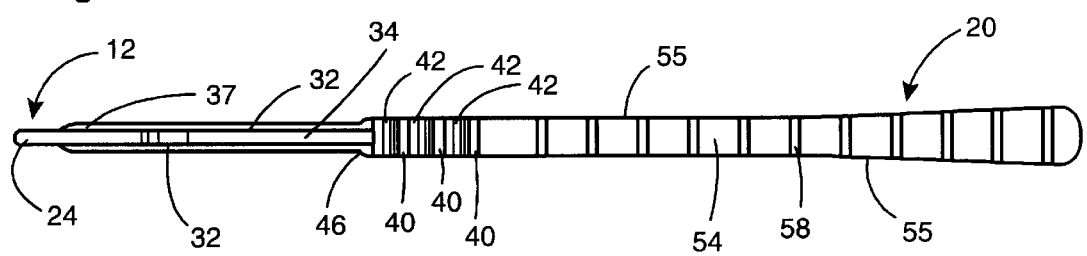
FIG. 4 discloses a bottom plan view of the invention.

Having reference to the drawings, attention is directed first to FIG. 1 which shows a surgical tool made in accordance with this present invention, with the surgical tool being designated by the numeral 10. This particular tool is known as an amniotic membrane perforator, and in this invention it is fabricated from an appropriate plastic, such as polystyrene. The tool is dimensioned such that the tool is flexible at the flex means.

The amniotic membrane perforator 10 of this invention has as its main components a tip portion 12, a shaft portion 15, flex means 17, and a handle portion 20. The shaft portion 15 is intermediate the tip portion 12 and the flex means 17. Similarly, the flex means 17 is intermediate the shaft portion 15 and the handle portion 20. Thus, it will be readily appreciated that the tip portion 12 and the handle portion 20 are at opposite ends of the tool 10.

As can best be appreciated from a comparison of FIGS. 1–4, the tip portion 12 is formed primarily of a disk-shaped member 22, which has a curved wall 24 extending from the top surface of the tip portion around to the front wall or tip end of the tip portion and thence around to the bottom surface of the tip portion. On the top surface of the tip portion 12 is a hook 25 which points upwardly and rearwardly towards the handle portion.

Extending from the region of the tip portion 12 rearwardly is shaft portion 15, which in the preferred embodiment of this invention is comprised generally of a vertical component 30 and a horizontal component 35. The vertical component 30 has a pair of side walls 32, a top 33 and a bottom 34. The side walls 32 of the vertical component are parallel to one another. The top 33 can best be viewed in FIG. 3, where it is shown located between the tip portion 12 and the horizontal component 35 of the shaft portion 15. It can be appreciated that its length is far less than that associated with the bottom 34.

Meanwhile, the horizontal component 35 is positioned atop most of the vertical component 30. The horizontal component 35 has a top 36 which is coextensive with the vertical component's top 33. The horizontal component 35 also has a bottom 37, best shown in FIG. 4, which extends on both sides of the vertical component 30. The bottom 37 is parallel to both the top 36, the top 33, and the bottom 34. The horizontal component 35 also has a pair of side edges 38, parallel to one another, which flare outwardly from the side walls 32 and extend rearwardly to flex means 17. In the preferred embodiment of the invention, the height of the side edges 38 is less than the height of the side walls 32. It should also be noted that the side walls 32 are coextensive with the side walls of the tip portion.

As can be appreciated from the drawing figures, immediately rearward of the shaft portion 15 is flex means 17. The flex means component of the invention permits, upon flexure, the shaft portion 15 to be pivoted relative to the handle portion, with that pivoting occurring at the flex means. Although there may be a variety of structures which could serve as flex means, in the preferred embodiment of the invention the flex means 17 is comprised of at least one crest 40 and at least one valley 42, and more preferably a plurality of both crests and valleys. As shown in the drawing figures, the most preferred embodiment of the invention has three crests and three valleys.

The crests 40 and valleys 42 have top and bottom surface portions 44 as well as side edges 45. The height of the side edges 45 is approximately the same as the height associated with side edges 38. From a comparison of FIGS. 3 and 4 it will be seen that the width of the horizontal component 35 is less than the width of the flex means 17. Between side edges 38 and side edges 45 are a pair of connecting edge portions 46.

As can be appreciated from the drawing figures, immediately rearward of the flex means 17 is the handle portion 20. The handle portion has a top surface 52, a bottom surface 54 and a pair of side edges 55. Both the top surface and bottom surface are parallel to one another, and are generally planar except for spaced apart upper ribs 57 and lower ribs 58. Each of the plurality of upper ribs 57 and lower ribs 58 extend across the handle portion from one side edge 55 to the side edge 55 on the opposite side of the handle portion. It will also be appreciated that the ribs alternate from the top surface 52 to the bottom surface 54. While the width of the handle portion immediately adjacent the flex means is the same as the width of the flex means, the width of the handle portion increases slightly as the handle extends rearwardly. Thus, in the preferred embodiment of the invention, the width of the handle is tapered, such that the width steadily increases. It will also be readily appreciated that the handle portion is wider than the handle portion is high.

Figure 5:
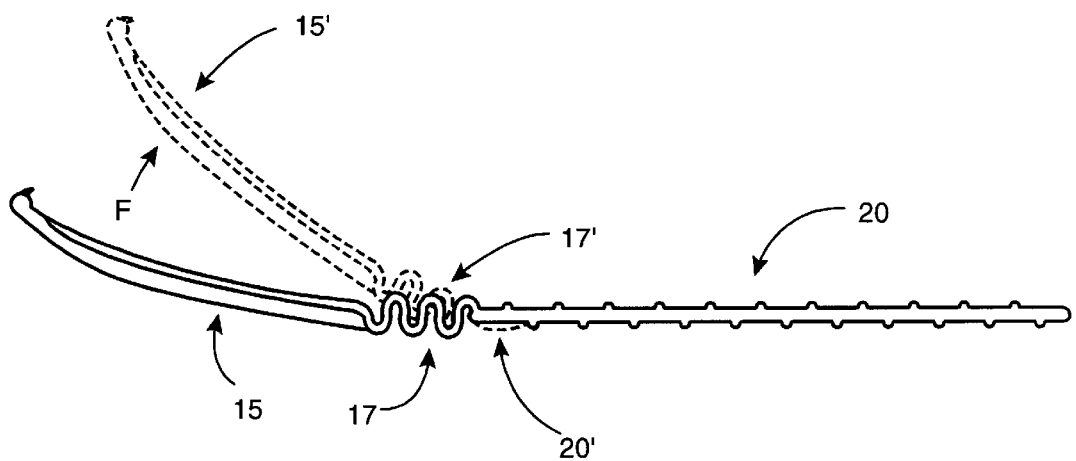
FIG. 5 discloses a side elevational view of the invention, shown in both its rest position and an operative position.

In actual use, the amniotic membrane perforator of this invention is shown in FIG. 5 as flexure in direction "F" causes the shaft portion 15 to pivot relative to the handle portion 20. In one such flexed position, the shaft portion 15 is shown as 15'. Similarly, the flex means 17 is shown as 17', and the handle portion 20 is shown as 20'. The flexible character of the tool permits the user to angle the tip potion to accommodate a patient's unique anatomic curve. When used, the medical professional places the tool in their hand such that the handle rests on their palm and the vertical component 30 is positioned intermediate two of their fingers. As the medical professional applies pressure in direction "F", the tool flexes such that the two crests closest to the handle converge on each other. As flexure continues, the distances of separation between each of the valleys 42 increase slightly. Thus the tool of this invention can easily flex at the flex means, so that the shaft portion pivots relative to the handle portion.

While the form of apparatus herein described constitutes a preferred embodiment of the invention, it is to be understood that the invention is not limited to this precise form of apparatus, and that changes may be made therein without departing from the scope of the invention which is defined in the appended claims.

What is claimed is:

1. An amniotic membrane perforator tool comprising,
   a tip portion, said tip portion having a hook,
   a shaft portion adjacent said tip portion, said shaft portion being of a generally T-shaped cross-section, said shaft portion having a vertical component and a horizontal component,
   flex means, said shaft portion being intermediate said tip portion and said flex means, and
   a handle portion, said flex means being intermediate said shaft portion and said handle portion, said shaft portion being pivotable at said flex means relative to said handle portion.

2. The tool according to claim 1 wherein said flex means comprises at least one crest and at least one valley.

3. The tool according to claim 2 wherein said flex means comprises a plurality of crests and valleys.

4. The tool according to claim 1 wherein said handle portion includes a plurality of ribs.

5. The tool according to claim 4 wherein said handle portion has a top surface, said top surface having a plurality of ribs.

6. The tool according to claim 4 wherein said handle portion has a bottom surface, said bottom surface having a plurality of ribs.

7. The tool according to claim 4 wherein said handle portion has a top surface and a bottom surface, said top surface and said bottom surface each having a plurality of ribs.

8. The tool according to claim 1 wherein said handle portion is wider than said handle portion is high.

9. An amniotic membrane perforator tool comprising,
   a tip portion, said tip portion having a hook,
   a shaft portion adjacent said tip portion, said shaft portion being of a generally T-shaped cross-section, said shaft portion having a vertical component and a horizontal component,
   flex means comprising at least one crest and at least one valley, said shaft portion being intermediate said tip portion and said flex means, and
   a handle portion, said handle portion being wider than said handle portion is high, said flex means being intermediate said shaft portion and said handle portion, said shaft portion being pivotable at said flex means relative to said handle portion.

10. The tool according to claim 9 wherein said flex means comprises a plurality of crests and valleys.

11. The tool according to claim 9 wherein said handle portion includes a plurality of ribs.

12. The tool according to claim 11 wherein said handle portion has a top surface, said top surface having a plurality of ribs.

13. The tool according to claim 11 wherein said handle portion has a bottom surface, said bottom surface having a plurality of ribs.

14. The tool according to claim 11 wherein said handle portion has a top surface and a bottom surface, said top surface and said bottom surface each having a plurality of ribs.

15. An amniotic membrane perforator tool comprising,
   a tip portion, said tip portion having a hook,
   a shaft portion adjacent said tip portion, said shaft portion being of a generally T-shaped cross-section, said shaft portion having a vertical component and a horizontal component,
   flex means comprising at least one crest and at least one valley, said shaft portion being intermediate said tip portion and said flex means, and
   a handle portion wider than said handle portion is high, said handle portion including a plurality of ribs, said flex means being intermediate said shaft portion and said handle portion, said shaft portion being pivotable at said flex means relative to said handle portion.

* * * * *